US010001441B2

(12) United States Patent
Nakanishi et al.

(10) Patent No.: US 10,001,441 B2
(45) Date of Patent: Jun. 19, 2018

(54) MODIFICATION PROCESSING DEVICE, MODIFICATION MONITORING DEVICE AND MODIFICATION PROCESSING METHOD

(71) Applicants: SCREEN Holdings Co., Ltd., Kyoto (JP); OSAKA UNIVERSITY, Osaka (JP)

(72) Inventors: Hidetoshi Nakanishi, Kyoto (JP); Akira Ito, Kyoto (JP); Iwao Kawayama, Suita (JP); Masayoshi Tonouchi, Suita (JP); Yuji Sakai, Suita (JP)

(73) Assignees: SCREEN HOLDINGS CO., LTD., Kyoto (JP); OSAKA UNIVERSITY, Osaka (JP)

( * ) Notice: Subject to any disclaimer, the term of this patent is extended or adjusted under 35 U.S.C. 154(b) by 0 days. days.

(21) Appl. No.: 14/866,835

(22) Filed: Sep. 25, 2015

(65) Prior Publication Data

US 2016/0093539 A1 Mar. 31, 2016

(30) Foreign Application Priority Data

Sep. 26, 2014 (JP) ................................. 2014-196295

(51) Int. Cl.
*G01J 5/02* (2006.01)
*G01N 21/64* (2006.01)
(Continued)

(52) U.S. Cl.
CPC ............ *G01N 21/6489* (2013.01); *G01J 1/42* (2013.01); *H01L 21/26* (2013.01); *H01L 22/12* (2013.01); *G01N 21/3586* (2013.01); *H01L 22/20* (2013.01)

(58) Field of Classification Search
CPC ...................... G01N 21/6489; G01N 21/3586
See application file for complete search history.

(56) References Cited

U.S. PATENT DOCUMENTS

| 6,081,127 A * | 6/2000 | Wagner .............. G01N 21/6489 |
| | | 324/754.23 |
| 7,943,533 B2 | 5/2011 | Mizuno |
| | (Continued) | |

FOREIGN PATENT DOCUMENTS

| JP | H01-239863 A | 9/1989 |
| JP | H05-094959 A | 4/1993 |
| | (Continued) | |

OTHER PUBLICATIONS

Office Action issued in corresponding Japanese Patent Application No. 2014-196295, dated Dec. 12, 2017 (w/partial English translation).

*Primary Examiner* — Kenneth J Malkowski
(74) *Attorney, Agent, or Firm* — McDermott Will & Emery LLP

(57) ABSTRACT

There is provided a technique for easily inspecting the modification state of a film in a semiconductor substrate. A modification processing device modifies a film by irradiating a semiconductor substrate with pulsed light emitted from a light irradiation part. The modification processing device includes an electromagnetic wave detection part for detecting an electromagnetic wave pulse including a millimeter wave or a terahertz wave radiated from the semiconductor substrate in response to the irradiation with the pulsed light. The modification processing device further includes a modification determination part for determining the modification state, based on the intensity of the electromagnetic wave pulse.

7 Claims, 7 Drawing Sheets

(51) Int. Cl.
*H01L 21/26* (2006.01)
*G01J 1/42* (2006.01)
*H01L 21/66* (2006.01)
*G01N 21/3586* (2014.01)

(56) References Cited

U.S. PATENT DOCUMENTS

| | | | |
|---|---|---|---|
| 8,129,683 | B2 | 3/2012 | Itsuji et al. |
| 2013/0015368 | A1* | 1/2013 | Nakanishi .......... G01N 21/3586 250/459.1 |
| 2013/0083319 | A1 | 4/2013 | Nakanishi et al. |
| 2013/0140288 | A1* | 6/2013 | Yu ..................... B23K 26/03 219/121.78 |

FOREIGN PATENT DOCUMENTS

| | | |
|---|---|---|
| JP | 2006-147848 A | 6/2006 |
| JP | 2008-004694 A | 1/2008 |
| JP | 2009-175127 A | 8/2009 |
| JP | 2011-014914 A | 1/2011 |
| JP | 2013-019861 A | 1/2013 |
| JP | Z013-072843 A | 4/2013 |
| JP | 2013-170864 A | 9/2013 |
| JP | 2014-078660 A | 5/2014 |

* cited by examiner

MODIFICATION PROCESSING DEVICE, MODIFICATION MONITORING DEVICE AND MODIFICATION PROCESSING METHOD

BACKGROUND OF THE INVENTION

Field of the Invention

The present invention relates to a process for modifying a film of a semiconductor substrate and, more particularly, to a technique for inspecting a modification state.

Description of the Background Art

During a manufacture of a semiconductor device, a film quality process for modifying the quality of a film of a semiconductor substrate by irradiating a surface of the semiconductor substrate with light has been performed (for example, as disclosed in Japanese Patent Application Laid-Open No. 2011-014914, Japanese Patent Application Laid-Open No. 2008-004694 and Japanese Patent Application Laid-Open No. 2014-078660).

Japanese Patent Application Laid-Open No. 2011-014914 discloses the technique of irradiating a silicon substrate with a pulsed laser having a pulse width of 10 to 1000 femtoseconds to activate impurities.

Japanese Patent Application Laid-Open No. 2008-004694 discloses the technique of modifying a surface of a GaN substrate by the use of an ultrashort pulsed laser such as a femtosecond laser. More specifically, Japanese Patent Application Laid-Open No. 2008-004694 discloses the technique of irradiating the surface of the GaN substrate with the pulsed laser to form an irregular structure, to form an amorphous region or a strain region and to relax a strain.

Japanese Patent Application Laid-Open No. 2014-078660 discloses the technique of heating a region implanted with impurity ions in a wide-gap semiconductor by laser annealing to activate the impurity ions.

Unfortunately, it has been necessary for the conventional techniques to repeatedly perform a modification process and the inspection of a modification state in alternate order to set conditions for light irradiation for the purpose of performing the modification process under preferable conditions. Thus, complicated operations and time-consuming feedback have been required for the optimization of the conditions for light irradiation.

SUMMARY OF THE INVENTION

The present invention is intended for a modification processing device for modifying a film by irradiating a semiconductor substrate with light.

According to the present invention, the modification processing device comprises: a light irradiation part for irradiating a semiconductor substrate with light; and an electromagnetic wave detection part for detecting the intensity of an electromagnetic wave including a millimeter wave or a terahertz wave radiated from the semiconductor substrate in response to the irradiation with light.

The modification processing device is capable of detecting a change in physical properties of the semiconductor substrate which results from modification by detecting the millimeter wave or the terahertz wave generated by the generation, disappearance and movement of photocarriers. Therefore, the modification processing device is capable of easily inspecting the modification state of the film in the semiconductor substrate while performing the modification process.

Preferably, the modification processing device further comprises a modification determination part for determining the modification state of a film of the semiconductor substrate, based on the intensity of the electromagnetic wave detected by the electromagnetic wave detection part.

The modification processing device is capable of easily inspecting the modification state by determining the modification state.

Preferably, the modification processing device further comprises a PL light detection part for detecting photoluminescent light radiated from a surface of the semiconductor substrate by the irradiation with light from the light irradiation part, wherein the modification determination part determines the modification of the semiconductor substrate, based on the intensity of the electromagnetic wave detected by the electromagnetic wave detection part and the photoluminescent light detected by the PL light detection part.

The modification processing device is capable of inspecting the modification state in further detail by detecting the photoluminescent light.

Preferably, the modification processing device further comprises an irradiation control part for controlling the irradiation with light for modifying the film of the semiconductor substrate, based on a result of determination of the modification determination part.

The modification processing device is capable of preferably controlling the irradiation with light for modification in accordance with the modification state.

Preferably, the light emitted from the light irradiation part is pulsed light which modifies the film of the semiconductor substrate and which generates an electromagnetic wave in the semiconductor substrate.

This simplifies the device configuration because the same pulsed light is used for the modification of the film and the generation of the electromagnetic wave.

The present invention is also intended for a modification monitoring device for monitoring the modification state of a film in a semiconductor substrate.

According to the present invention, the modification monitoring device comprises an electromagnetic wave detection part for detecting an electromagnetic wave including a millimeter wave or a terahertz wave radiated from said semiconductor substrate in response to a irradiation with light.

The modification monitoring device is capable of inspecting the modification state of the film in the semiconductor substrate, based on the intensity of the millimeter wave or the terahertz wave.

The present invention is also intended for a method of modifying a film by irradiating a semiconductor substrate with light.

According to the present invention, the method comprises the steps of: (a) irradiating a semiconductor substrate with light for modifying a film; and (b) detecting the intensity of an electromagnetic wave including a millimeter wave or a terahertz wave radiated from the semiconductor substrate in response to the irradiation with light in the step (a).

It is therefore an object of the present invention to provide a technique for easily inspecting the modification state of a film of a semiconductor substrate.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
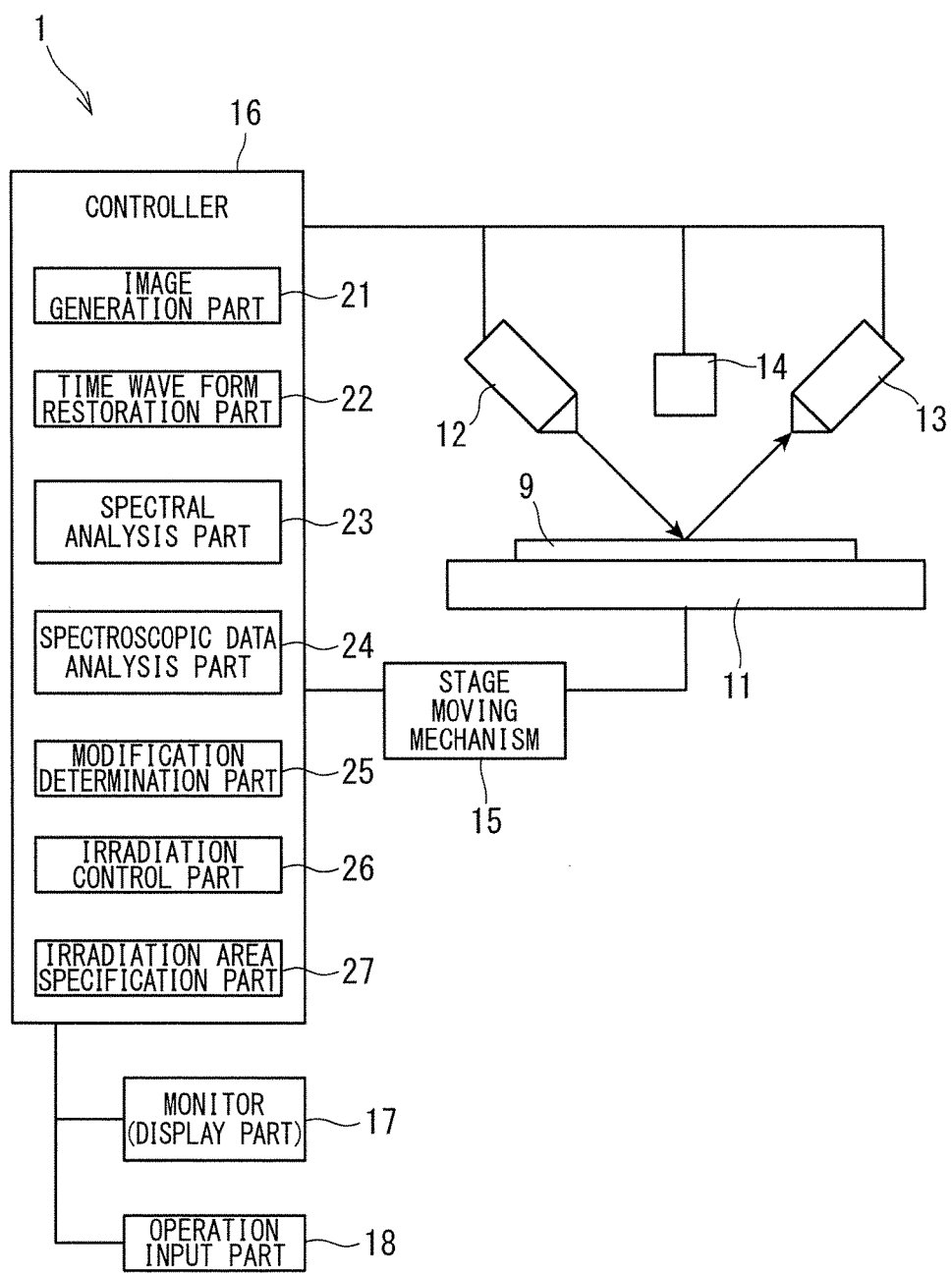
FIG. 1 is a schematic block diagram of a modification processing device according to a first preferred embodiment of the present invention.

Preferred embodiments according to the present invention will now be described with reference to the accompanying drawings. Components described in the preferred embodiments are merely illustrative, and there is no intention to limit the scope of the present invention thereto. In the drawings, the dimensions of components and the number of components are shown in exaggeration or in simplified form, as appropriate, for the sake of easier understanding.

1. First Preferred Embodiment

<1.1. Configuration of Modification Processing Device 1>

FIG. 1 is a schematic block diagram of a modification processing device 1 according to a first preferred embodiment of the present invention. The modification processing device 1 is a device for modifying a film in a semiconductor substrate 9 including a semiconductor.

A semiconductor, as used herein, includes silicon (Si), germanium (Ge), compound semiconductors such as gallium arsenide (GaAs), and wide-gap semiconductors having a bandgap greater than that of Si, such as gallium nitride (GaN) and silicon carbide (SiC). The first preferred embodiment will be described on the assumption that a SiC Schottky barrier diode is formed or is to be formed in the semiconductor substrate 9.

Figure 2:
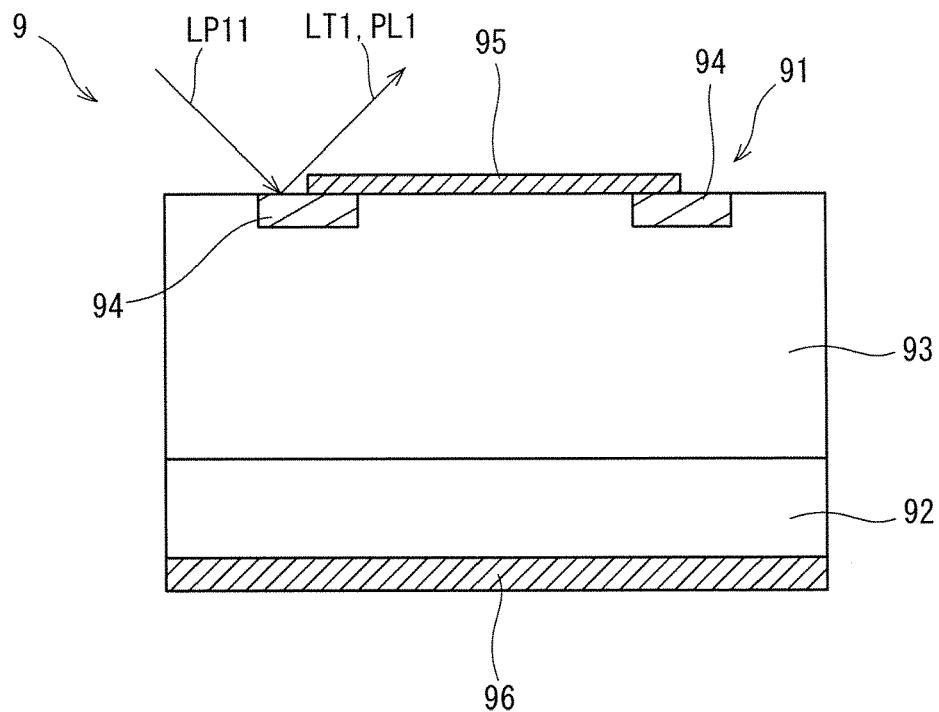
FIG. 2 is a schematic sectional view showing a SiC Schottky barrier diode formed in a semiconductor substrate.
Figure 3:
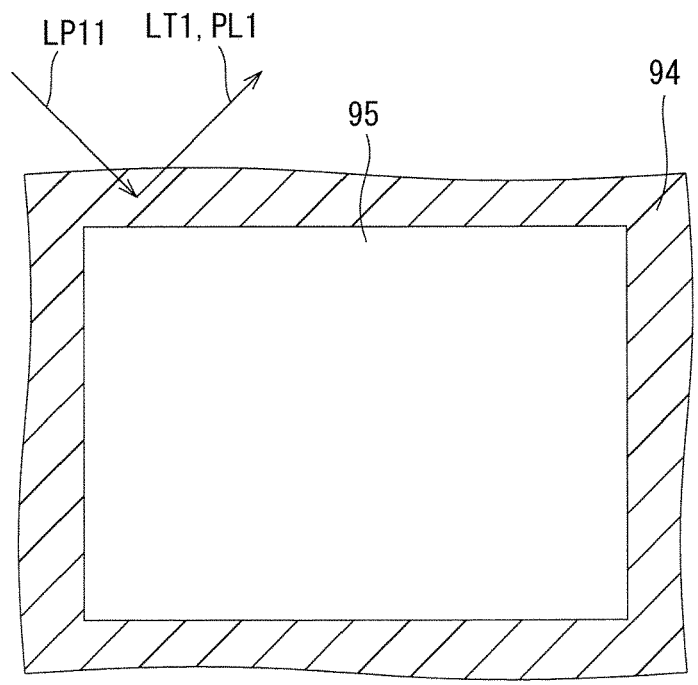
FIG. 3 is a schematic plan view showing the SiC Schottky barrier diode.

FIG. 2 is a schematic sectional view showing a SiC Schottky barrier diode 91 formed in the semiconductor substrate 9. FIG. 3 is a schematic plan view showing the SiC Schottky barrier diode 91. In the SiC Schottky barrier diode 91, an n-type SiC drift layer 93 serving as a withstand voltage layer for holding a withstand voltage is provided by epitaxial growth on an n-type semiconductor substrate 92 including an n-type low-resistance impurity such as N (nitrogen) and P (phosphorus).

A p-type region 94 is formed in an upper part of the drift layer 93 by doping with a p-type impurity such as B (boron) and Al (aluminum). The p-type region 94 is formed by implanting p-type impurity ions from over the drift layer 93 and thereafter performing a heat treatment (annealing process) step for activation of the impurity ions. The modification processing device 1 is configured to be capable of performing the aforementioned annealing process for the formation of the p-type region 94.

An anode electrode 95 is provided on the drift layer 93. A cathode electrode 96 is provided under the semiconductor substrate 92. The anode electrode 95 serves as a Schottky electrode for the drift layer 93. The p-type region 94 are positioned in a peripheral edge part of the anode electrode 95, and serves as a guard ring region provided for the purpose of preventing electric field concentration in the vicinity of the peripheral edge part of the anode electrode 95. A region of an upper surface of the drift layer 93 where the p-type region 94 is not formed functions as a Schottky barrier diode.

Referring again to FIG. 1, the modification processing device 1 includes a stage 11, a light irradiation part 12, an electromagnetic wave detection part 13, a photoluminescent light (referred to hereinafter as "PL light") detection part 14, a stage moving mechanism 15, a controller 16, a monitor 17 and an operation input part 18.

The stage 11 holds the semiconductor substrate 9 on the stage 11 by the use of a required fixing element. Conceivable examples of the fixing element include holding tools for holding the semiconductor substrate 9 therebetween, an adhesive sheet for affixing the semiconductor substrate 9 thereto to fix the semiconductor substrate 9, and a suction hole for fixing the semiconductor substrate 9 by suction. Of course, other fixing elements capable of fixing the semiconductor substrate 9 may be used.

Figure 4:
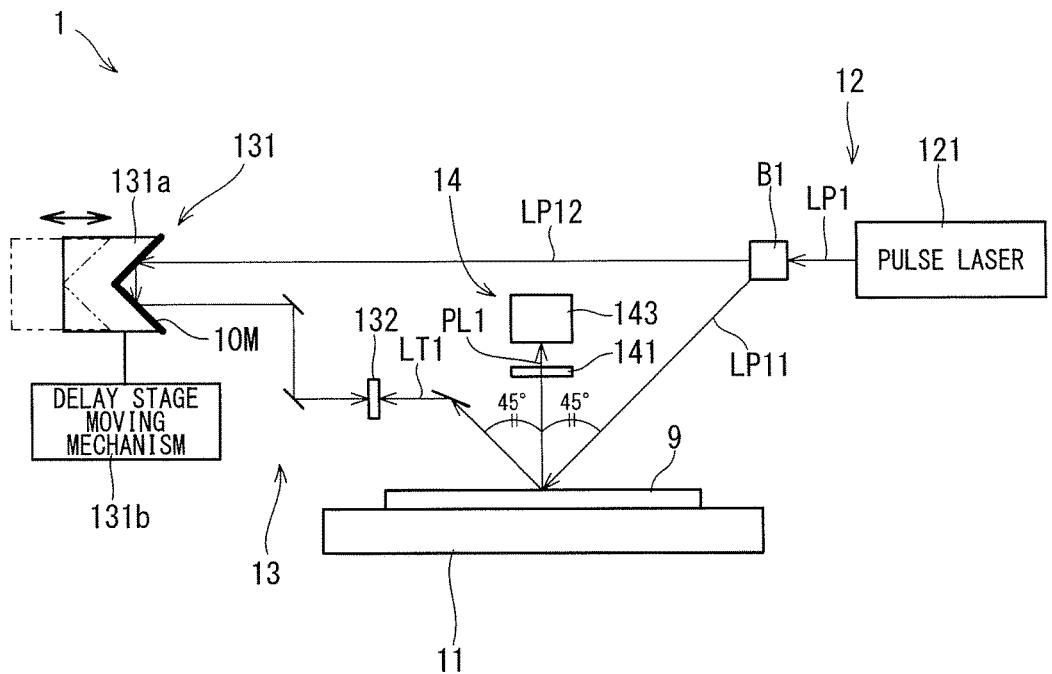
FIG. 4 is a schematic block diagram of a light irradiation part and an electromagnetic wave detection part according to the first preferred embodiment.

FIG. 4 is a schematic block diagram of the light irradiation part 12 and the electromagnetic wave detection part 13 according to the first preferred embodiment. The light irradiation part 12 includes a pulse laser 121. The pulse laser 121 preferably emits laser light (pulsed light LP1) having a pulse width of 1 femtosecond to 10 picoseconds.

The beam of pulsed light LP1 emitted from the pulse laser 121 is split into two beams of pulsed light by a beam splitter B1. One of the two beams of pulsed light is pulsed light LP11 which passes through an optical system such as a lens to impinge on the semiconductor substrate 9. Thus, the annealing process is performed.

In the example shown in FIG. 1 or 4, the semiconductor substrate 9 is irradiated with the pulsed light LP11 so that the optical axis of the pulsed light LP11 is incident obliquely on a main surface of the semiconductor substrate 9. More specifically, the irradiation angle of the pulsed light LP11 is set so that the incident angle thereof is 45 degrees. The incident angle of the pulsed light LP11, however, is not limited to such an angle but may be varied within a range of 0 to 90 degrees, as appropriate. The pulsed light LP11 need not necessarily impinge upon the front surface of the semiconductor substrate 9 but may impinge on a side surface or the back surface of the semiconductor substrate 9.

As shown in FIG. 2 or 3, the irradiation of the p-type region 94, that is, the front surface of the SiC Schottky barrier diode 91 with the pulsed light LP11 with the intention of performing the annealing process generates an electromagnetic wave pulse LT1. Photocarriers (free electrons and holes) generated by the irradiation of the p-type region 94 of the SiC Schottky barrier diode 91 with the pulsed light LP11 are accelerated by a depletion layer of a pn junction and an internal electric field present at a Schottky junction, so that a photoelectric current is generated and disappears instantaneously. According to Maxwell's equations, when a change occurs in current, an electromagnetic wave having an intensity proportional to the time derivative of the current is generated. The electromagnetic wave pulse LT1 generated from the p-type region 94 includes a millimeter wave (30 to 300 GHz) or a terahertz wave (0.1 to 30 THz). The generated electromagnetic wave pulse LT1 is detected by the electromagnetic wave detection part 13 to be described later in detail.

The other of the two beams of pulsed light produced by the beam splitter B1 is detection pulsed light LP12 which passes via a delay part 131, mirrors and the like, and enters a detector 132. The electromagnetic wave pulse LT1 generated in response to the irradiation with the pulsed light LP11 is concentrated by a parabolic mirror (not shown), passes via a mirror and the like, and enters the detector 132.

The detector 132 serves as an electromagnetic wave detection element including, for example, a photoconductive switch. It is assumed that the detection pulsed light LP12 enters the detector 132 at the instant when the electromagnetic wave pulse LT1 enters the detector 132. Then, a current in accordance with the electric field strength of the electromagnetic wave pulse LT1 is generated instantaneously in the photoconductive switch. The current in accordance with the electric field strength is converted through an I/V conversion circuit, an A/D conversion circuit and the like into a digital quantity. In this manner, the electromagnetic wave detection part 13 detects the electric field strength of the electromagnetic wave pulse LT1 generated in the semiconductor substrate 9 in response to the irradiation with the detection pulsed light LP12. Other elements, e.g. an element to which a non-linear optical crystal is applied, may be used for the detector 132.

The delay part 131 includes a delay stage 131a and a delay stage moving mechanism 131b. The delay part 131 is an optical element for continuously changing the time of arrival of the detection pulsed light LP12 from the beam splitter B1 at the detector 132. The delay stage 131a is linearly moved in the incident direction of the detection pulsed light LP12 by the delay stage moving mechanism 131b. The delay stage 131a includes a reflecting mirror 10M for reflecting the detection pulsed light LP12 back in the incident direction.

More specifically, the delay stage moving mechanism 131b drives the delay stage 131a, based on the control of the controller 16. Then, the delay stage 131a moves linearly in the incident direction of the detection pulsed light LP12, and the reflecting mirror 10M accordingly moves linearly. Thus, the optical path length of the detection pulsed light LP12 is precisely changed.

The delay stage 131a changes a time difference between the instant at which the electromagnetic wave pulse LT1 arrives at the electromagnetic wave detection part 13 (detector 132) and the instant at which the detection pulsed light LP12 arrives at the electromagnetic wave detection part 13 (detector 132). Thus, the delay stage 131a changes the optical path length of the detection pulsed light LP12 to thereby delay the time (detection time, sampling time, or phase) at which the electric field strength of the electromagnetic wave pulse LT1 is detected by the electromagnetic wave detection part 13 (detector 132).

Other techniques may be used to change the time of arrival of the detection pulsed light LP12 at the detector 132. Specifically, an electro-optical effect may be used. That is, an electro-optical element with a refractive index changed by changing the voltage applied thereto may be used as a delay element. Specifically, an electro-optical element disclosed in Japanese Patent Application Laid-Open No. 2009-175127 may be used.

Alternatively, a delay part for changing the optical path length of the pulsed light LP11 or the optical path length of the electromagnetic wave pulse LT1 radiated from the semiconductor substrate 9 may be provided. In this case, the instant at which the electromagnetic wave pulse LT1 arrives at the detector 132 may be shifted relative to the instant at which the detection pulsed light LP12 arrives at the detector 132. This delays the time at which the electric field strength of the electromagnetic wave pulse LT1 is detected by the detector 132.

The PL light detection part 14 includes a spectroscope 141 and a light detector 143. The light detector 143 is formed by a photodiode. The recombination of the photocarriers generated in the SiC Schottky barrier diode 91 due to irradiation with the pulsed light LP11 generates PL light PL1. The PL light detection part 14 detects the generated PL light PL1.

Figure 5:
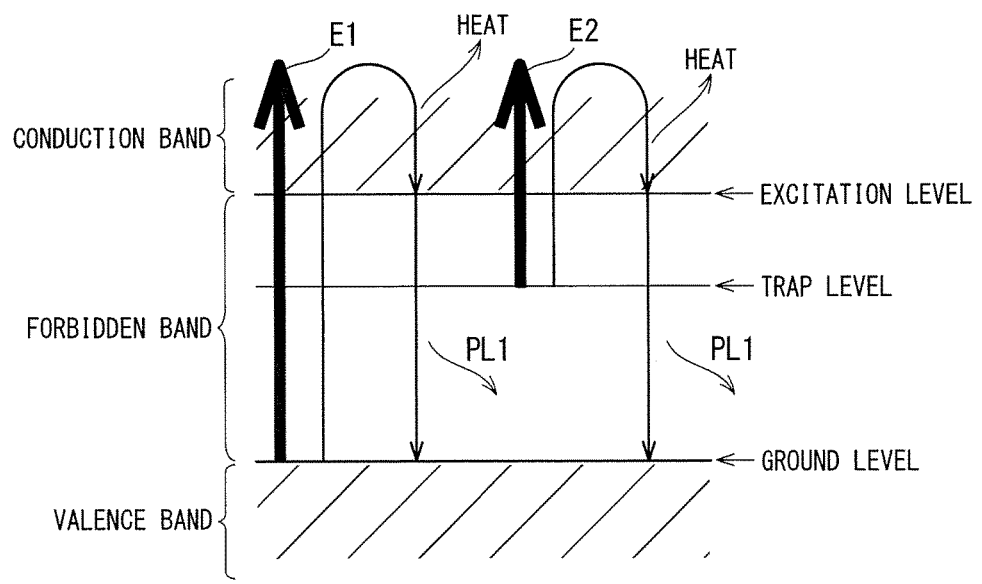
FIG. 5 is a schematic view showing a band structure of the semiconductor substrate.

FIG. 5 is a schematic view of a band structure of the semiconductor substrate 9. For the annealing process, the pulsed light LP11 having energy E1 exceeding the excitation level is emitted from the ground level which is the energy gap of the semiconductor (in this case, SiC) constituting the semiconductor substrate 9, as shown in FIG. 5. Thus, heat and the PL light PL1 are generated when the excited photocarriers make a transition to the ground level. The p-type region 94 is annealed by the generated heat.

A relation between bandgap energy Eg and the wavelength λ (nm) of light is expressed as "λ=hc/Eg". For example, the bandgap of 4H-SiC is 3.26 eV. The wavelength absorbed by this semiconductor is less than 380 nm.

As shown in the right-hand part of FIG. 5, the annealing process by the use of the pulsed light LP11 having a wavelength which is energy E2 lower than the energy E1 exceeding the forbidden band may be performed by using a trap level resulting from impurities and defects. That is, it is only necessary that the energy of light is converted into heat, and the pulsed light LP11 for modification need not necessarily have the wavelength of the energy equal to or greater than the bandgap.

The amount of heat generated is dependent on the intensity (the number of photons) of the pulsed light LP1. Decrease in the intensity of the pulsed light LP1 for irradiation allows the generation of the electromagnetic wave pulse LT1 and the PL light while preventing the annealing from proceeding. This achieves the inspection of the modification state of the film of the semiconductor substrate 9, based on the electromagnetic wave pulse LT1 or the PL light PL1.

Referring again to FIG. 1, the stage moving mechanism 15 includes an X-Y table for moving the stage 11 in a two-dimensional plane. The stage moving mechanism 15 drives the X-Y table to move the semiconductor substrate 9 held on the stage 11 relative to the light irradiation part 12. Thus, by the provision of the stage moving mechanism 15, the modification processing device 1 is capable of moving the semiconductor substrate 9 to any position in the two-dimensional plane. This allows the pulsed light LP11 to scan a region (to-be-annealed region) required to be annealed in the semiconductor substrate 9, for example. Also, the stage 11 may be moved manually, with the driving source of the stage moving mechanism 15 dispensed with.

The stage moving mechanism 15 is an example of a scanning mechanism. For example, a moving element for moving the light irradiation part 12 in a two-dimensional plane may be provided in place of or in addition to moving the semiconductor substrate 9. In either case, the irradiation of the to-be-annealed region in the semiconductor substrate 9 with the pulsed light LP11 is achieved. It is also contemplated that a region to be inspected is scanned by the pulsed light LP11 by changing the optical path of the pulsed light LP11. Specifically, it is contemplated that a galvanometer mirror is provided to cause the pulsed light LP11 to scan in two directions parallel to the surface of the semiconductor substrate 9 and orthogonal to each other. It is also contemplated that a polygon mirror, a piezoelectric mirror, an acousto-optical element or the like is used in place of the galvanometer mirror.

The controller 16 is configured as a typical computer including a CPU, a ROM, a RAM and an auxiliary storage part (for example, a hard disk). The controller 16 is connected to the pulse laser 121 of the light irradiation part 12, the delay stage 131a and the detector 132 of the electromagnetic wave detection part 13, the PL light detection part 14 and the stage moving mechanism 15. The controller 16 controls the operations of these components and receives data from these components.

More specifically, the controller 16 receives data about the electric field strength of the electromagnetic wave pulse LT1 from the detector 132, for example. The controller 16 also controls the delay stage moving mechanism 131b for moving the delay stage 131a. Further, the controller 16 receives data about the position of the delay stage 131a, such as a distance of movement of the reflecting mirror 10M, from a linear scale provided in the delay stage 131a and the like.

The controller 16 includes an image generation part 21, a time wave form restoration part 22, a spectral analysis part 23, a spectroscopic data analysis part 24, a modification determination part 25, an irradiation control part 26 and an irradiation area specification part 27. These parts may be functions implemented by the CPU in the controller 16 operating in accordance with programs or be formed by purpose-built circuits in the form of hardware.

The image generation part 21 generates an electric field strength distribution image which presents a distribution of the electric field strength of the electromagnetic wave pulse LT1 generated from the semiconductor substrate 9 in visual form. In this electric field strength distribution image, differences in electric field strength are represented visually using different colors, shades of color or different patterns.

The time wave form restoration part 22 restores the time wave form of the electromagnetic wave pulse LT1, based on the electric field strength of the electromagnetic wave pulse LT1 detected by the electromagnetic wave detection part 13 (detector 132). Specifically, the time wave form restoration part 22 moves the reflecting mirror 10M of the delay stage 131a to change the optical path length (optical path length of a first optical path) of the detection pulsed light LP12, thereby changing the time of arrival of the detection pulsed light LP12 at the detector 132. This changes the time (phase) at which the detector 132 detects the electric field strength of the electromagnetic wave pulse LT1. The time wave form restoration part 22 detects the electric field strength of the electromagnetic wave pulse LT1 for each phase. The detected electric field strengths are plotted along the time axis. Thus, the time wave form restoration part 22 restores the time wave form of the electromagnetic wave pulse LT1.

The spectral analysis part 23 performs a spectral analysis on the restored electromagnetic wave pulse LT1. Specifically, the spectral analysis part 23 performs Fourier transformation on the time wave form restored by the time wave form restoration part 22 to acquire an amplitude intensity spectrum for each frequency.

Figure 6:
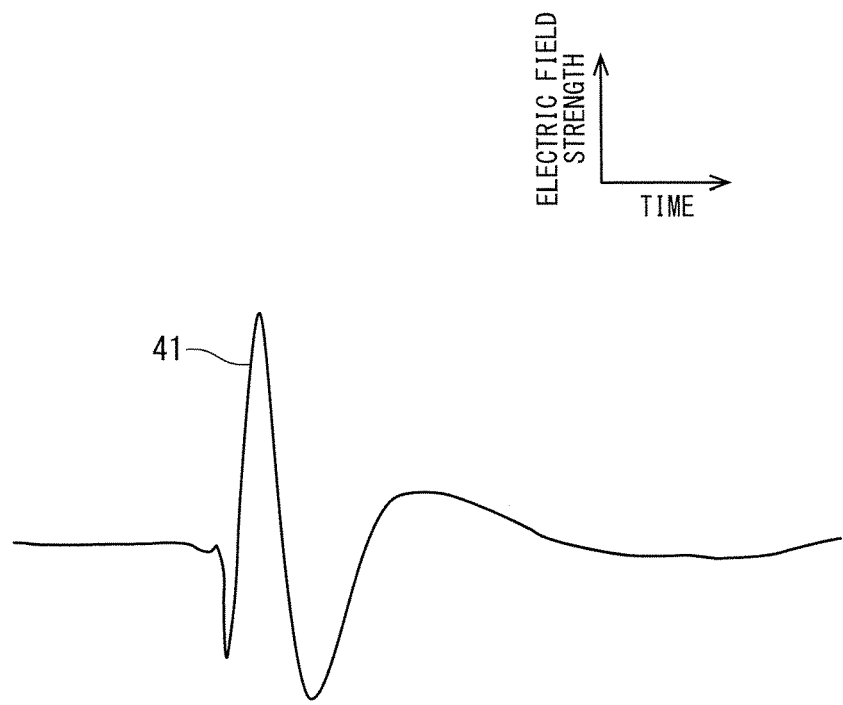
FIG. 6 is a graph showing an example of the time wave form of an electromagnetic wave pulse.
Figure 7:
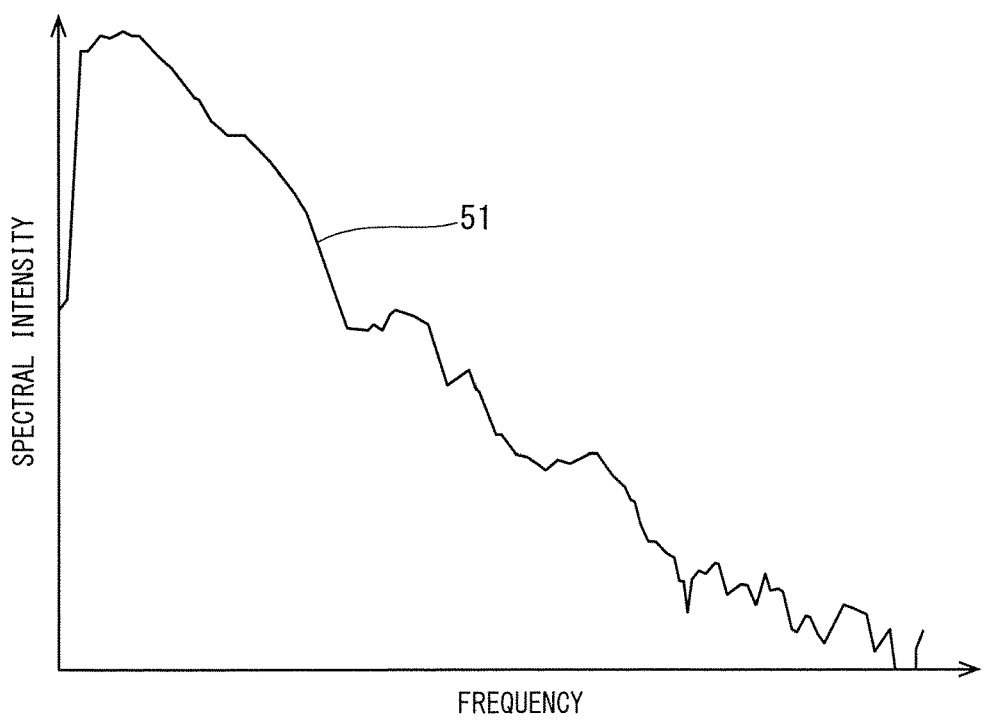
FIG. 7 is a graph showing an example of a spectral distribution of the electromagnetic wave pulse.

FIG. 6 is a graph showing an example of a time wave form 41 of the electromagnetic wave pulse LT1. FIG. 7 is a graph showing an example of a spectral distribution 51 of the electromagnetic wave pulse LT1. The spectral distribution 51 shown in FIG. 7 is obtained by performing Fourier transformation on the time wave form 41 shown in FIG. 6. For example, the analysis of the spectral distributions of the electromagnetic wave pulse LT1 generated from the semiconductor substrate 9 before and after the annealing process of the semiconductor substrate 9 provides the more detailed analysis of changes in electric field strength of the electromagnetic wave pulse LT1 which the modification state provided by the annealing process is reflected.

The spectroscopic data analysis part 24 analyzes the PL light PL1 detected by the PL light detection part 14. Specifically, the spectroscopic data analysis part 24 acquires the intensity (wavelength profile) for each wavelength of the PL light PL1 detected by the PL light detection part 14. The acquisition of the wavelength profile of the PL light PL1 achieves the analysis of the modification state provided by the annealing process. As the annealing process proceeds, the intensity or wavelength of the generated PL light PL1 is changed. Thus, the modification state of the film is suitably seized by monitoring the intensity or wavelength of the PL light PL1.

The modification determination part 25 determines whether the modification of the film of the semiconductor substrate 9, i.e. the annealing process, is completed or not, based on the intensity of the electromagnetic wave pulse LT1 detected by the detector 132.

After the film is modified by the annealing process, the intensities of the electromagnetic wave pulse LT1 and the PL light PL1 generated are changed. For example, the modification of the p-type region 94 changes the characteristics of a p-n junction or a p-metal junction. This changes the intensity of the generated electromagnetic wave pulse LT1. That is, the modification state is suitably seized by monitoring the intensity of the electromagnetic wave pulse LT1 while performing the annealing process.

The modification state of the film irradiated with the pulsed light LP11 is monitored by the provision of the electromagnetic wave detection part 13. Thus, the electromagnetic wave detection part 13 may be interpreted as a modification monitoring device. A combination of the modification determination part 25, the PL light detection part 14 and the spectroscopic data analysis part 24 in addition to the electromagnetic wave detection part 13 may be interpreted as a modification monitoring device.

In the present preferred embodiment, the modification determination part 25 determines whether the annealing process is completed or not, based on the intensity of the electromagnetic wave pulse LT1 generated from the semiconductor substrate 9 during the annealing process. A conceivable example of this determination method includes making a comparison between the intensity of the detected electromagnetic wave pulse LT1 and a predetermined threshold value of the intensity of the electromagnetic wave pulse LT1 assumed that the annealing process is completed.

The modification determination part 25 also determines the modification of the semiconductor substrate 9, based on the PL light PL1 detected by the PL light detection part 14. More specifically, the modification determination part 25 monitors the intensity or wavelength of the PL light PL1 acquired by the spectroscopic data analysis part 24 during the annealing process. It can be considered that the modification determination part 25 determines that the annealing process is completed when the intensity or wavelength of the PL light PL1 is changed to that obtained after the modification.

The irradiation control part 26 controls the irradiation of the semiconductor substrate 9 with the pulsed light LP11, based on the result of determination of the modification determination part 25. Specifically, for example, when the modification determination part 25 determines that the annealing process of a region irradiated with the pulsed light LP11 is completed, the irradiation control part 26 stops the irradiation of the region with the pulsed light LP11. A conceivable example of the method of stopping the irradiation with the pulsed light LP11 includes stopping the emission of light from the light irradiation part 12 by intercepting light on the optical path of the pulsed light LP1 or the pulsed light LP11. Another conceivable example of the method includes moving the semiconductor substrate 9 to change the irradiation position of the pulsed light LP11 to a different position. In this manner, the irradiation control part 26 is capable of completing the annealing process at a preferable time by stopping the irradiation with the pulsed light LP11, based on the result of determination of the modification determination part 25.

Alternatively, the irradiation control part 26 may control the amount of light per unit area so as to increase or decrease, for example, without completely stopping the irradiation with the pulsed light LP11. Specifically, the irradiation control part 26 may control the light irradiation part 12 so as to increase or decrease the amount of light per unit area of the pulsed light LP11 when the intensity of the electromagnetic wave pulse LT1 is higher or lower than a predefined threshold value.

Also, the irradiation control part 26 may control the light irradiation part 12 so as to stop the irradiation with the pulsed light LP11 or to increase or decrease the amount of light per unit area, based on the intensity or wavelength of the PL light PL1.

The irradiation area specification part 27 specifies an area of the film to be modified. More specifically, for the annealing process of the semiconductor substrate 9, the irradiation area specification part 27 specifies the position of the anode electrode 95 serving as an interconnect line portion in the semiconductor substrate 9 from a circuit diagram. Then, the irradiation area specification part 27 specifies an area around the anode electrode 95 as an irradiation area to be irradiated with the pulsed light LP11 for the purpose of forming the p-type region 94. The irradiation control part 26 irradiates the irradiation area specified by the irradiation area specification part 27 with the pulsed light LP11.

<1.2. Modification Process>

Figure 8:
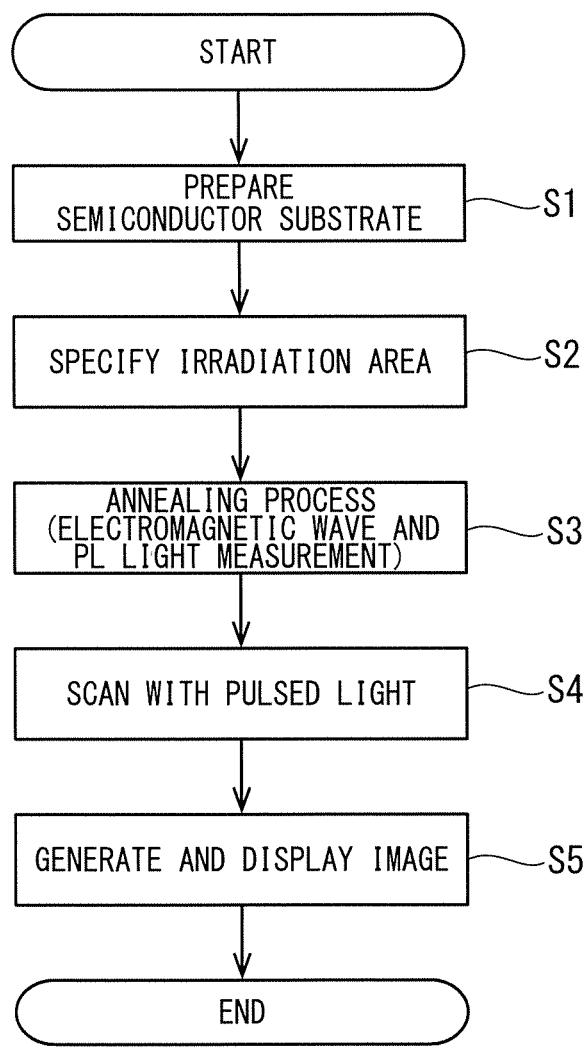
FIG. 8 is a flow diagram for illustrating a modification process performed by the modification processing device according to the first preferred embodiment.

FIG. 8 is a flow diagram for illustrating the modification process performed by the modification processing device 1 according to the first preferred embodiment. The operations of the modification processing device 1 are performed under the control of the controller 16, unless otherwise specified.

First, the step of preparing the semiconductor substrate 9 is performed (Step S1). In this step, the semiconductor substrate 9 is transported onto the stage 11, and is held on the stage 11. Then, alignment is performed, as appropriate.

After the preparation of the semiconductor substrate 9 is completed, the irradiation area to be irradiated with the pulsed light LP11 is specified (Step S2). Specifically, the position in which the p-type region 94 is to be formed is specified by specifying the position of the interconnect line portion from a circuit diagram represented by CAD data and the like. This specified position is defined as the irradiation area.

After the specification of the irradiation area is completed, the annealing process is performed (Step S3). Specifically, the semiconductor substrate 9 is moved so that the specified irradiation area coincides with the irradiation position of the pulsed light LP11. The annealing process is performed by irradiation with the pulsed light LP11. While the annealing process is being performed, the detection of the electromagnetic wave pulse LT1 generated from the semiconductor substrate 9 by the irradiation with the pulsed light LP11 and the detection of the PL light PL1 are performed.

As mentioned above, the irradiation with the pulsed light LP11 is performed based on the control of the irradiation control part 26. Specifically, when the annealing process at a specific location proceeds, the modification determination part 25 determines whether the modification is made or not, based on the intensity of the electromagnetic wave pulse LT1 and the intensity or wavelength profile of the PL light PL1. When the modification determination part 25 determines that the modification is completed, the irradiation control part 26 changes the irradiation position of the pulsed light LP11 or stops the emission of light from the light irradiation part 12 to thereby stop the irradiation with the pulsed light LP11. The annealing process is performed in this manner.

After the annealing process is completed, the modification processing device 1 scans the semiconductor substrate 9 with the pulsed light LP11 for the purpose of inspecting the semiconductor substrate 9 (Step S4). In Step S4, the range to be scanned is arbitrarily determined, but the region subjected to the annealing process in Step S3 by the pulsed light LP11, for example, is scanned. Then, information about the intensity of the electromagnetic wave pulse LT1 generated is collected.

For the collection of the information about the electromagnetic wave pulse intensity, the intensity of the electromagnetic wave pulse LT1 at a single certain detection time (phase) may be detected while the delay stage 131a is fixed. Alternatively, the intensity of the electromagnetic wave pulse LT1 may be detected at a plurality of detection times. For the detection of the intensity at the plurality of detection times, the same region may be scanned a plurality of times at respective different detection times. Alternatively, the electromagnetic wave pulse LT1 may be measured at the plurality of detection times by irradiation with the pulsed light LP11 while the delay stage 131a is moved to predefined positions at each inspection points of the region during the single scanning of the region.

After the scanning in Step S4 is completed, the modification processing device 1 generates and displays an image (Step S5). Specifically, the image generation part 21 generates an electromagnetic wave intensity distribution image, based on electromagnetic wave intensity data collected in Step S4. The generated image is displayed on the monitor 17.

The generation and display of the electromagnetic wave intensity distribution image as in Step S4 and Step S5 allows the semiconductor substrate 9 after the annealing process to be inspected for various defects (inclusion of impurities, cracks, electrode formation failures and the like). It should be noted that Steps S4 and S5 may be dispensed with. Also, a region of the semiconductor substrate 9 other than the region subjected to the annealing process may be inspected in Steps S4 and S5.

The time wave form (with reference to FIG. 6) of the electromagnetic wave pulse LT1 may be restored at any time before, during and after the annealing process. The frequency analysis of the electromagnetic wave pulse LT1 may be performed by doing Fourier transformation on the restored time wave form.

As described above, the electromagnetic wave pulse LT1 is detected in the modification processing device 1 while the annealing process is performed. The detection of the electromagnetic wave pulse LT1 allows the quantitative measurements of the generation, recombination and movement of photocarriers or changes in the electrical conductivity of an electrically conductive film. Thus, the modification state of the semiconductor substrate 9 provided by the annealing process is suitably monitored by monitoring these parameters.

Also, the PL light PL1 is detected in the modification processing device 1 while the annealing process is performed. The PL light PL1 is light emitted when excited electrons and holes are recombined together. That is, the measurement of the PL light PL1 allows the quantitative analysis of the characteristics of the semiconductor substrate 9 such as band-to-band recombination, recombination between a band and a trap level and recombination between trap levels. Thus, the modification state of the semiconductor substrate 9 provided by the annealing process is suitably seized.

As mentioned above, the modification processing device 1 is capable of monitoring the intensity of the electromagnetic wave pulse LT1 and the intensity or wavelength of the PL light PL1. This allows the inspection of the modification state of the film, so that the annealing process is performed under preferable conditions. Also, the modification processing device 1 is capable of inspecting the modification state in a non-contacting manner. Thus, the semiconductor substrate 9 need not be transported to the outside for the inspection. This reduces the danger of damages to the semiconductor substrate 9 to achieve the inspection of the modification state easily.

2. Second Preferred Embodiment

Next, a second preferred embodiment according to the present invention will be described. In the following description, components having the same functions as those described above are designated by like reference numerals and characters or like reference numerals and characters with alphabetic characters appended thereto, and will not be described in detail in some cases.

Figure 9:
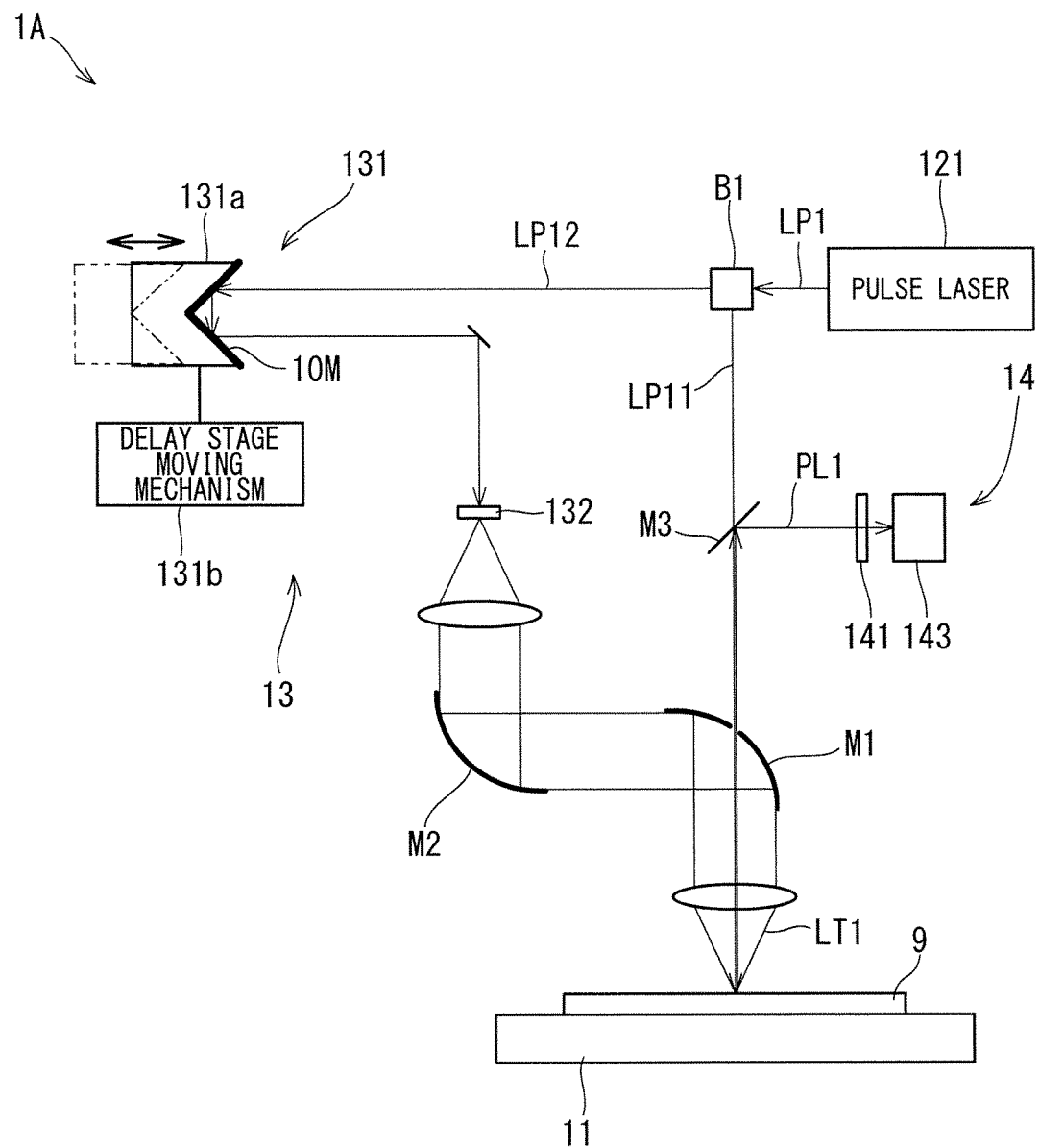
FIG. 9 is a schematic block diagram of the modification processing device according to a second preferred embodiment of the present invention.

FIG. 9 is a schematic block diagram of a modification processing device 1A according to the second preferred embodiment. In the modification processing device 1A, the pulsed light LP11 passes through a hole formed in a parabolic mirror M1 and impinges perpendicularly on the main surface of the semiconductor substrate 9. Thus, the annealing process for the formation of the p-type region 94 is performed locally. The electromagnetic wave pulse LT1 generated in response to the irradiation with the pulsed light LP11 and emitted on the main surface side irradiated with the pulsed light LP11 is concentrated by parabolic mirrors M1 and M2 and detected by the detector 132. Part of the PL light PL1 generated in response to the irradiation with the pulsed light LP11 and radiated in a direction coaxial with the optical axis of the pulsed light LP11 passes through the hole in the parabolic mirror M1, is reflected from a half mirror M3, enters the spectroscope 141, and is detected by the light detector 143.

Like the modification processing device 1 of the first preferred embodiment, the modification processing device 1A is capable of acquiring the intensity of the electromagnetic wave pulse LT1 and the intensity or wavelength of the PL light PL1 during the annealing process. This allows the inspection of the modification state of the film, so that the annealing process is performed under preferable conditions. Also, the modification processing device 1A is capable of inspecting the modification state in a non-contacting manner. Thus, the semiconductor substrate 9 need not be transported to the outside for the inspection. This reduces the danger of damages to the semiconductor substrate 9 to achieve the inspection of the modification state easily.

3. Third Preferred Embodiment

Figure 10:
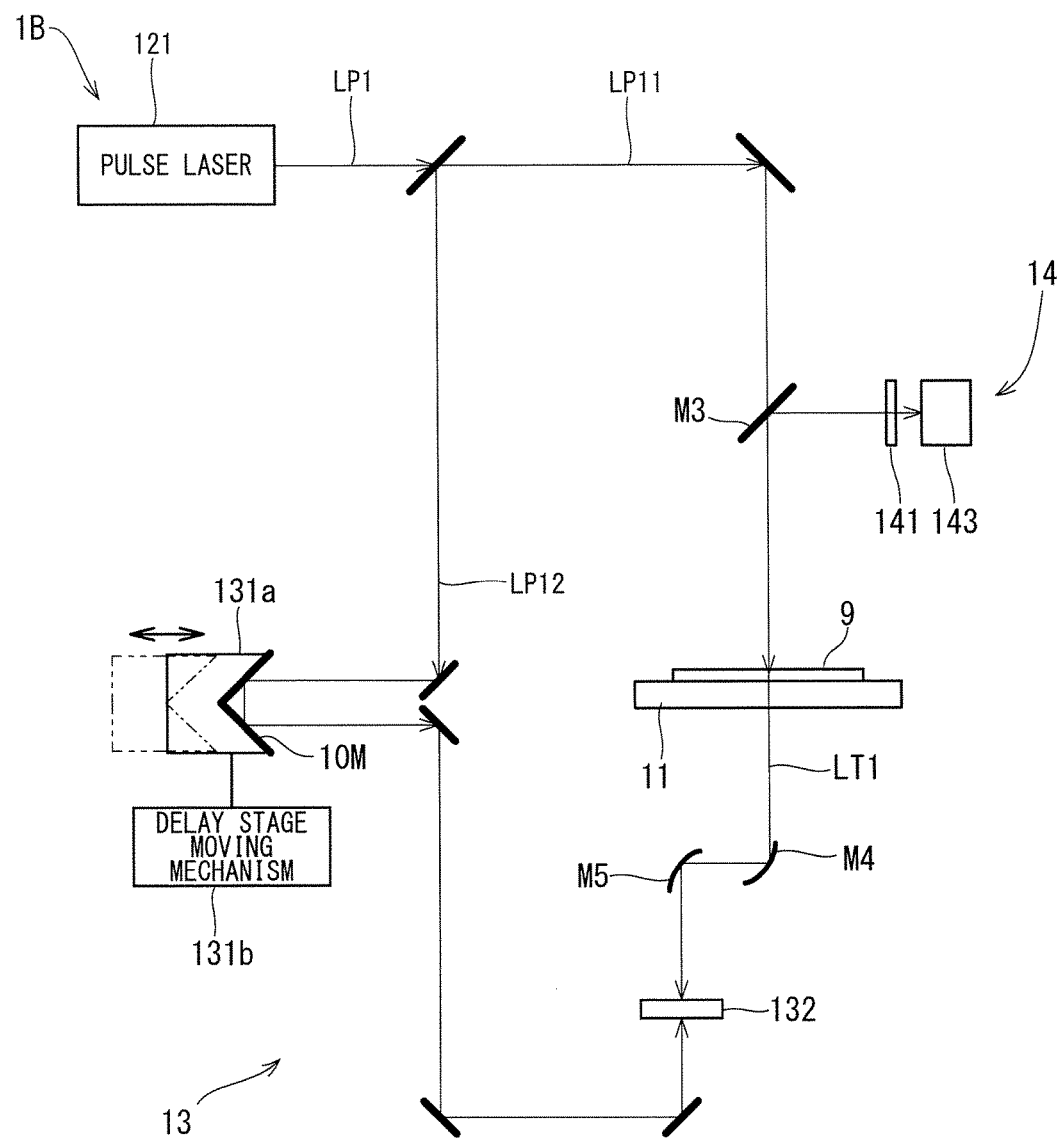
FIG. 10 is a schematic block diagram of the modification processing device according to a third preferred embodiment of the present invention.

FIG. 10 is a schematic block diagram of a modification processing device 1B according to a third preferred embodiment of the present invention. In the modification processing device 1B, the pulsed light LP11 impinges perpendicularly on the main surface of the semiconductor substrate 9. Thus, the annealing process for the formation of the p-type region 94 is performed locally. Part of the electromagnetic wave pulse LT1 generated in response to the irradiation with the pulsed light LP11 and transmitted through the semiconductor substrate 9 toward the back surface side of the semiconductor substrate 9 is concentrated by parabolic mirrors M4 and M5 and detected by the detector 132. Part of the PL light PL1 generated in response to the irradiation with the pulsed light LP11 and radiated in a direction coaxial with the optical axis of the pulsed light LP11 is reflected from the half mirror M3, enters the spectroscope 141, and is detected by the light detector 143.

Like the modification processing device 1 of the first preferred embodiment, the modification processing device 1B is capable of monitoring the intensity of the electromagnetic wave pulse LT1 and the intensity or wavelength of the PL light PL1 during the annealing process. This allows the inspection of the modification state of the film, so that the annealing process is performed under preferable conditions. Also, the modification processing device 1B is capable of inspecting the modification state in a non-contacting manner. Thus, the semiconductor substrate 9 need not be transported to the outside for the inspection. This reduces the danger of damages to the semiconductor substrate 9 to achieve the inspection of the modification state easily.

4. Modifications

In the modification processing device 1, the light irradiation part 12 irradiates the semiconductor substrate 9 with the pulsed light LP11 for the annealing process. However, the light irradiation part 12 may irradiate the semiconductor substrate 9 with other types of light.

For example, the light irradiation part 12 may be designed to perform flash lamp annealing. In this case, the light irradiation part 12 irradiates the semiconductor substrate 9 with a flash of light, and irradiates the semiconductor substrate 9 with the pulsed light LP11 separately. This achieves the generation of the electromagnetic wave pulse LT1 and the PL light PL1 while performing the annealing process.

Two light sources which emit two beams of continuous light slightly different in oscillation frequency from each other may be used in place of the pulse laser 121 to generate an electromagnetic wave (as disclosed in Japanese Patent Application Laid-Open No. 2013-170864). Specifically, the two beams of continuous light are superimposed by means of a coupler formed by an optical fiber such as an optical waveguide to generate an optical beat signal corresponding to the difference frequency. This optical beat signal is caused to impinge on the semiconductor substrate 9, so that an electromagnetic wave corresponding to the frequency of the optical beat signal is radiated.

The modification processing device 1 may include a spectroscope and a light detector for detecting Raman scattered light. The Raman scattered light includes various pieces of information about the molecular state of the semiconductor substrate 9. Thus, the modification state provided by the annealing process is inspected by analyzing the Raman scattered light.

In the preferred embodiments, the annealing process in the field of semiconductor manufacture is described as the process for modifying the film in the semiconductor substrate 9. The process for modifying the film is not limited to the annealing process, but includes other processes. For example, a surface treatment for forming an uneven structure resulting from ablation on a surface, and a process for crystallizing an amorphous material are included in the modification process.

Further, the modification processing device 1 may use other types of semiconductor devices or semiconductor wafers as the semiconductor substrate. The modification processing device 1 may process a semiconductor substrate having no electrodes formed thereon.

While the invention has been described in detail, the foregoing description is in all aspects illustrative and not restrictive. It is understood that numerous other modifications and variations can be devised without departing from the scope of the invention.

What is claimed is:

1. A modification processing device for modifying a film by irradiating a semiconductor substrate with light, comprising:
   a light irradiation part for irradiating a semiconductor substrate with light for modifying said film;
   an electromagnetic wave detection part for detecting the intensity of an electromagnetic wave including a millimeter wave or a terahertz wave radiated from said semiconductor substrate in response to the irradiation with light for modifying said film;
   a modification determination part for determining the modification state of said film of said semiconductor substrate, based on changes generated due to modification of said film proceeded by the irradiation with said light in the intensity of said electromagnetic wave detected by said electromagnetic wave detection part; and
   an irradiation control part for controlling the irradiation with light for modifying said film of said semiconductor substrate, based on a result of determination of said modification determination part.

2. The modification processing device according to claim 1, further comprising
   a PL light detection part for detecting photoluminescent light radiated from a surface of said semiconductor substrate by the irradiation with light from said light irradiation part,
   wherein said modification determination part determines the modification of said semiconductor substrate, based on the intensity of the electromagnetic wave detected by said electromagnetic wave detection part and said photoluminescent light detected by said PL light detection part.

3. The modification processing device according to claim 1, wherein
   the light emitted from said light irradiation part is pulsed light which modifies the film of said semiconductor substrate and which generates an electromagnetic wave in said semiconductor substrate.

4. The modification processing device according to claim 1, wherein
   when said modification determination part determines that the modification of said film of a region irradiated with said light is completed, said light irradiation part stops the irradiation with said light.

5. A modification processing method of modifying a film by irradiating a semiconductor substrate with light, comprising the steps of:
   (a) irradiating a semiconductor substrate with light for modifying a film;
   (b) detecting the intensity of an electromagnetic wave including a millimeter wave or a terahertz wave radiated from said semiconductor substrate in response to the irradiation with light for modifying said film in said step (a);
   (c) determining the modification state of said film of said semiconductor substrate, based on changes generated due to modification of said film proceeded by the irradiation with said light in the intensity of said electromagnetic wave detected in said step (b); and
   (d) controlling the irradiation with light for modifying said film of said semiconductor substrate, based on a result of determination in said step (c).

6. The modification processing method according to claim 5, wherein
   when said step (c) determines that the modification of said film of a region irradiated with said light is completed, the irradiation with said light in said step (a) is stopped.

7. A non-transitory, computer-readable medium encoded with executable instructions that, when executed by one or more processors, cause a modification processing device to perform operations comprising:
   irradiating, for a first period of time, a first area of a film of a semiconductor substrate with light for modifying the film of the semiconductor substrate;
   detecting a first intensity of an electromagnetic wave at a first time within the first period of time and a second intensity of the electromagnetic wave at a second time within the first period of time, wherein the electromagnetic wave is generated from radiation of the light from the first area of the film of the semiconductor substrate during the first period of time;
   determining a modification state of the film of the semiconductor substrate based on changes between the first intensity and the second intensity of the detected electromagnetic wave during the first period of time; and
   adjusting the irradiation with the light for modifying the film of the semiconductor substrate according to a result of the determination of the modification state of the film of the semiconductor substrate.

* * * * *